United States Patent [19]

Zaiger

[11] Plant 5,112

[45] Sep. 27, 1983

[54] INTERSPECIFIC ROOTSTOCK TREE 4-G-816

[76] Inventor: Chris F. Zaiger, 537 Rosemore Ave., Modesto, Calif. 95351

[21] Appl. No.: 373,252

[22] Filed: Apr. 29, 1982

[51] Int. Cl.[3] ..... A01H 5/03
[52] U.S. Cl. ..... Plt./38
[58] Field of Search ..... Plt./38, 42

*Primary Examiner*—Robert E. Bagwill
*Attorney, Agent, or Firm*—Roger B. Webster

[57] ABSTRACT

An interspecific (plum-peach) rootstock tree which is medium size, semi-vigorous, upright, medium dense, and well anchored by a semi-fibrous root system; foliated with medium size, elliptic leaves having a serrulate margin, medium length petiole, and medium size, globose, usually alternate glands positioned on base of blade and adjacent portion of the petiole; and flowers from medium size, plump buds; the flowers being large, showy, and pink but staminate, usually lacking or with incomplete pistils resulting in the tree being unfruitful.

1 Drawing Figure

BACKGROUND OF THE VARIETY

1. Field of the Invention

In the course of my activities in the field of horticultural genetics, and especially in respect to the hybridizing of new and distinct varieties of fruit and nut trees, I conduct such activities at my premises located near Modesto, Stanislaus County, Calif., and at which location I operate and maintain an experimental orchard, and wherein the present variety of rootstock tree was originated by me.

2. Classification of the Variety

The present variety of rootstock tree is embraced by Class 38, Plants, of the U.S. Patent Office Manual of Classification.

3. Prior Varieties

Among existing varieties of rootstock trees which are known to me, and mentioned herein, are the *Prunus besseyi* and *Prunus tomentosa* semi-dwarfing rootstocks (both unpatented) and Nemaguard rootstock (unpatented). The Red Beaut plum (U.S. Plant Pat. No. 2,539) is also identified in this specification.

ORIGIN OF THE VARIETY

The present variety of interspecific (plum-peach) rootstock tree was originated by me, in my aforesaid experimental orchard, as follows:

An open-pollinated seedling of the Red Beaut plum was grown in a large container, and—upon maturity—was placed, during the blooming season, in an orchard plot of certain peach selections. Thereafter, and when such plum seedling was mature, seed was collected therefrom and subsequently such seed produced a number of open-pollinated seedlings—four of which were determined to be crossed with peaches. Such determination was made from my observation of the shape and size of the leaves, the shape, size, and color of the flowers, the texture of the bark, and the tree growth habit. Upon continued observation and comparative testing of such four seedlings, one—and which is the present variety—evidenced substantial potential as a rootstock tree, and hence was selected for asexual reproduction.

ASEXUAL REPRODUCTION OF THE VARIETY

Subsequent to its origination and selection, I successfully asexually reproduced—in such experimental orchard—the present variety of rootstock tree by cuttings, budding, and grafting, and which reproductions, in maturity, ran true to the original tree in all respects.

SUMMARY OF THE VARIETY

The present variety of interspecific (plum-peach) rootstock tree is medium size, semi-vigorous, upright, medium dense, and well anchored by a semi-fibrous root system; foliated with medium size, elliptic leaves having a serrulate margin, medium length petiole, and medium size, globose, usually alternate glands positioned on base of blade and adjacent portion of the petiole; and flowers from medium size, plump buds; the flowers being large, showy, and pink but staminate, usually lacking or with incomplete pistils resulting in the tree being unfruitful.

The present variety, when used as a rootstock, is more particularly characterized as follows:

The present rootstock has a distinct dwarfing effect on the budded scion (such as peaches and nectarines), reducing the size of the resultant tree, in maturity, to approximately thirty-five percent of the mature tree size from the same scion on Nemaguard rootstock. Also, uniformity of tree size is greatly improved when the scion is grown on the present rootstock as compared, for example, to *Prunus besseyi* and *Prunus tomentosa.*

There is more uniform compatibility and a smoother union between the present rootstock and the scion than is provided by the semi-dwarfing rootstock, *Prunus besseyi* and *Prunus tomentosa;* the latter being propagated from seed, whereas the present rootstock is clonally propagated from cuttings.

The present rootstock produces little to no root or trunk suckers, whereas *Prunus besseyi* and *Prunus tomentosa* sucker extensively from root and trunk. Additionally, the upright growth of the present rootstock facilitates preparation of the cuttings prior to budding of the scion; this in comparison to the bushy growth of *Prunus besseyi* and which requires more attention. Further, the leaves of the present rootstock are, in the succulent stage, reddish bronze, and which color makes nursery cultural practices easier and more economical in comparison to the green-leaf *Prunus besseyi* and *Prunus tomentosa.*

The present rootstock grows successfully from dormant cuttings planted directly in the field, and—with a semi-fibrous root system having downward growth—is well anchored in the soil and as compared to *Prunus*

*besseyi* which usually is weak-rooted and poorly anchored.

The fruit of scion trees grown on the present rootstock matures earlier (two-three days), is approximately one-eighth larger in size, and has an increase of one to one and one-half percent in soluble solids; all as compared to the same scion tree grown on Nemaguard rootstock.

BRIEF DESCRIPTION OF THE DRAWING

The drawing is an illustration, by photographic reproduction in color, of a typical specimen of the foliage of the variety, with the upper and lower surfaces of the leaves being shown; a section of trunk (including the bud union) from a six-year old budded tree, the view—wherein the rootstock portion is shown uppermost—showing the uniformity of such bud union; and a section of branch from a three-year old tree of the variety, the view showing the color and characteristics of the rough bark.

DESCRIPTION OF THE VARIETY

The botanical details of the present new and distinct variety of interspecific (plum-peach) rootstock tree — with color definitions in common color terms, except where otherwise indicated—are as follows:

Tree:
- *Size.*—Medium.
- *Vigor.*—Semi-vigorous.
- *Form.*—Upright.
- *Density.*—Medium dense.
- *Use.*—Dwarfing rootstock, especially for peaches and nectarines.
- *Root system.*—Type: Semi-fibrous, but with a downward growth habit which provides good anchorage.

Trunk:
- *Size.*—Medium.
- *Texture.*—Shaggy.

Branches:
- *Size.*—Medium.
- *Texture.*—Rough.
- *Color.*—Brown to reddish brown.

Leaves:
- *Size.*—Medium. Average length — 6". Average width — $1\frac{5}{8}$".
- *Form.*—Elliptic. Tip acuminate. Base cuneate.
- *Margin.*—Serrulate.
- *Petiole.* 13 Medium size. Average length — $\frac{5}{8}$". Average width — 1/16". Longitudinally grooved.
- *Glands.*—Globose. Medium size. Number — 1 to 4 — average — 2. Positioned on base of blade and adjacent portion of petiole. Usually alternate.
- *Color*.*—Upper surface: Immature leaves — Reddish green to greenish gray. Mature leaves — Dark green (26-F-5 to 26-F-4). Lower surface: Immature leaves — Reddish gray green. Mature leaves — Grayish green to dull green (26-E-4 to 26-E-5).

*Reinhold Color Atlas by A. Korneruf and J. H. Wanscher

Flower buds:
- *Size.*—Medium.
- *Form.*—Plump.

Flowers:
- *Size.*—Large. Showy.
- *Blooming period.*—Mar. 5th–Mar. 12th, 1980 Variable with climatic conditions.
- *Pollen.*—Present.
- *Pistils.*—Incomplete to wanting. When present, approximately 150 normal size in relation to flower.
- *Color.*—Pink.

Fruit: Unfruitful on account of staminate flowers.

The herein described interspecific (plum-peach) rootstock tree may vary in slight detail due to climatic and soil conditions under which the variety may be grown; the present description being of the variety as grown in the Central Valley of California.

I claim:

1. A new and distinct variety of interspecific (plum-peach) rootstock tree substantially as illustrated and described; the variety being particularly characterized by its ability to reproduce by cuttings planted directly in the field, and—when used as a rootstock for peaches and nectarines—creates dwarfism and, with substantial uniformity, reduces the size of the scion tree to approximately thirty-five percent of the normal height of the same scion tree budded on Nemaguard rootstock; and further characterized by being well anchored, producing few root and trunk suckers, and influences the fruit of the scion tree to attain, in comparison to budding on Nemaguard rootstock, earlier maturity by two to three days, approximately one-eighth larger size, and an increase of one to one-and-one-half percent in soluble solids.

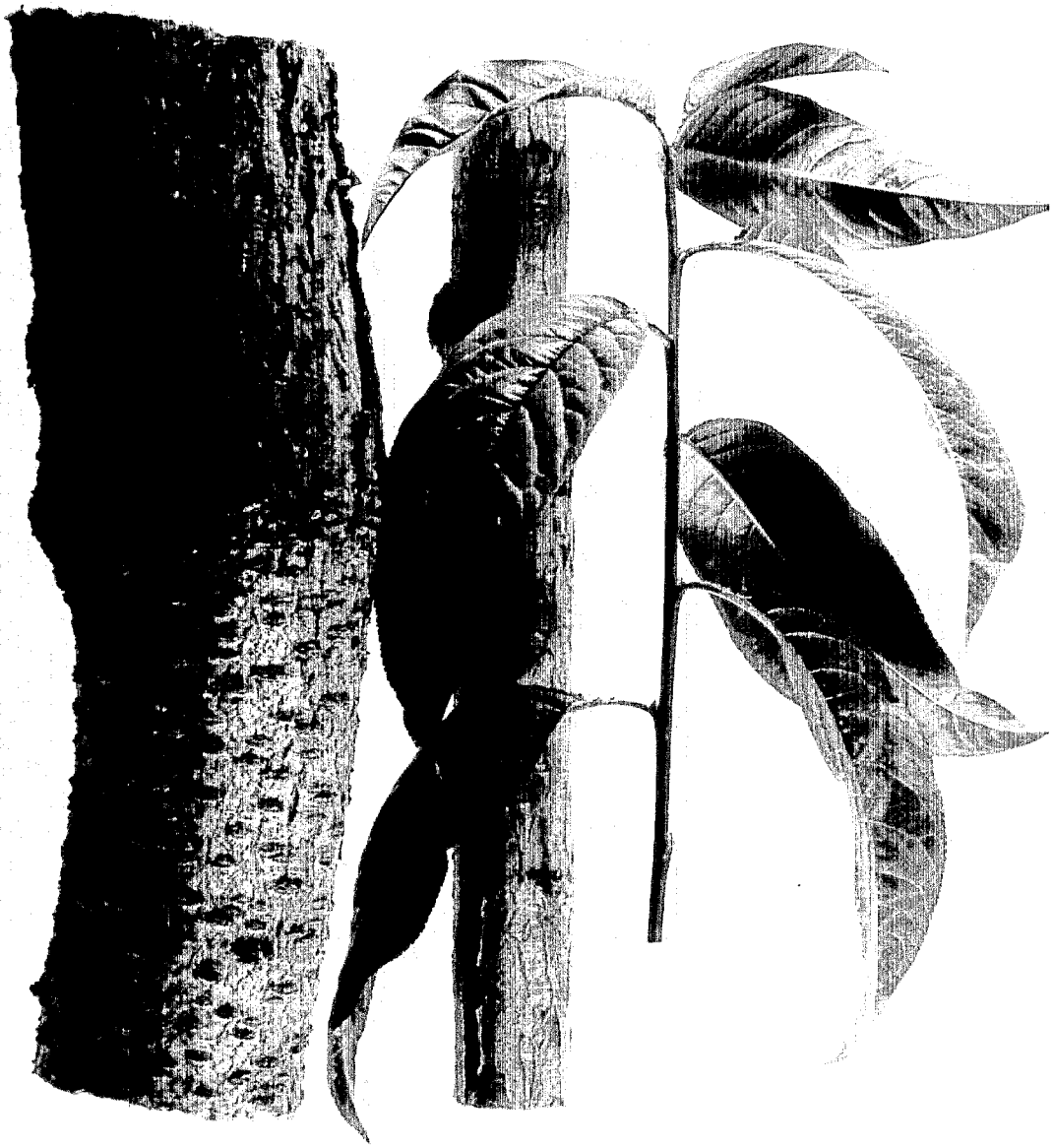

* * * * *